United States Patent
Rubod et al.

(10) Patent No.: US 12,042,179 B2
(45) Date of Patent: Jul. 23, 2024

(54) OBSTETRICAL INSTRUMENT OF THE FORCEPS TYPE FOR EXTRACTING A FETUS AND AN ASSISTANCE DEVICE FOR EXTRACTION EQUIPPED WITH AFOREMENTIONED FORCEPS

(71) Applicant: CHRU DE LILLE, Lille (FR)

(72) Inventors: Chrystèle Rubod, Lille (FR); Michel Cosson, Lille (FR); Estelle Jean, Lille (FR); Franck Gaultier, Lille (FR); Mathias Brieu, Lille (FR)

(73) Assignee: CHRU DE LILLE, Lille (FR)

( * ) Notice: Subject to any disclaimer, the term of this patent is extended or adjusted under 35 U.S.C. 154(b) by 504 days.

(21) Appl. No.: 17/251,807

(22) PCT Filed: Jun. 13, 2019

(86) PCT No.: PCT/IB2019/054939
§ 371 (c)(1),
(2) Date: Dec. 13, 2020

(87) PCT Pub. No.: WO2019/239362
PCT Pub. Date: Dec. 19, 2019

(65) Prior Publication Data
US 2021/0113242 A1  Apr. 22, 2021

(30) Foreign Application Priority Data

Jun. 15, 2018 (FR) ...................... 18 70712

(51) Int. Cl.
*A61B 17/44* (2006.01)
*A61B 17/00* (2006.01)

(52) U.S. Cl.
CPC ..... *A61B 17/44* (2013.01); *A61B 2017/00119* (2013.01); *A61B 2017/00221* (2013.01); *A61B 2017/445* (2013.01)

(58) Field of Classification Search
CPC . A61B 17/44; A61B 17/442; A61B 2017/445; A61B 2017/447; A61B 17/28–30
(Continued)

(56) References Cited

U.S. PATENT DOCUMENTS 3,785,381 A    1/1974  Lower et al.
6,440,089 B1 * 8/2002  Shine ............... A61B 5/033
                                              600/591

(Continued)

FOREIGN PATENT DOCUMENTS

WO    2004/108010 A2    12/2004
WO    2010/043860 A1    4/2010

OTHER PUBLICATIONS

Moreau, R et al. A method to evaluate skill transfer and acquisition of obstetric gestures based on the curvatures analysis of the position and the orientation. Journal of Biomedical Informatics, vol. 41, No. 6, Dec. 2008, pp. 991-1000 [online], [retrieved on Apr. 6, 2023]. (Year: 2008).*

*Primary Examiner* — Kathleen S Holwerda
*Assistant Examiner* — Serenity A Miller
(74) *Attorney, Agent, or Firm* — H&I PARTNERS; Chai Im; C. Andrew Im

(57) ABSTRACT

An assistance device and an associated obstetrical instrument, in particular of the forceps type, for extracting a fetus during childbirth having two branches. Each branch being equipped at one end with a gripping handle and at the other end with cephalic blades. The instrument further includes a measurement device using the blades and connector between the measurement device and the blade. The measurement device includes: a pressure measurement instrument configured to measure the pressure exerted by the blade on the fetus, a position measuring instrument to measure the positioning of the obstetrical instrument, a power supply, and a (Continued)

transmitter configured to transmit the measurements to a processing unit.

9 Claims, 1 Drawing Sheet

(58) Field of Classification Search
USPC .......................................... 606/122; 600/588
See application file for complete search history.

(56) References Cited

U.S. PATENT DOCUMENTS

| | | | |
|---|---|---|---|
| 9,554,828 B2 | 1/2017 | Paltieli | |
| 2002/0065519 A1* | 5/2002 | Vines | A61B 17/442 606/123 |
| 2011/0245865 A1* | 10/2011 | Harper | A61B 17/442 606/205 |
| 2012/0172890 A1* | 7/2012 | Paltieli | A61B 34/20 606/122 |
| 2013/0046303 A1* | 2/2013 | Evans | A61B 18/1445 606/45 |
| 2018/0243027 A1* | 8/2018 | Soni | A61B 18/1445 |

* cited by examiner

OBSTETRICAL INSTRUMENT OF THE FORCEPS TYPE FOR EXTRACTING A FETUS AND AN ASSISTANCE DEVICE FOR EXTRACTION EQUIPPED WITH AFOREMENTIONED FORCEPS

RELATED APPLICATIONS

This application is a § 371 application of PCT/IB2019/054939 filed Jun. 13, 2019, which claims priority from French Patent Application No. 18 70712 filed Jun. 15, 2018, each of which is incorporated herein by reference in its entirety.

TECHNICAL FIELD

The invention lies in the technical field of obstetric surgery and more particularly in assisting childbirth using an obstetrical instrument of the forceps type.

Although particularly provided in the shape of a forceps, the obstetrical instrument may also take the shape of other types of gripping clamps allowing extraction of the fetus by pulling operations at the fetal head and for example in the shape of a spatula.

BACKGROUND OF THE INVENTION

Many types of forceps or spatulas are known to date, these instruments, in their current shapes, were mainly developed and improved at the end of the 19th century and allow to facilitate the extraction of the fetus by vaginal route. The ends of these instruments (in particular cephalic blades) allow to ensure the grip on the fetus and have shapes adapted to limit the risk of injury to both the fetus and the mother. However, no obstetrical instrument allows to evaluate in real time the force exerted on the head of the fetus so that, in particular given the time or space constraints for the correct positioning of the forceps, it is common for the forceps to exert too much pressure on the fetus. Too much tightening of the blades can lead to bone lesions of the skull, in particular bone fractures in the parietal or frontal area. It can also lead to cranial nerve palsy and damage to the eye. For the practitioner, the only way to control the pressure is his own assessment, which depends mainly on many manikin trainings and his previous birth experience.

To limit the risk of injury, more and more caesarean sections are used, however the use of forceps remains in many cases preferable as cesarean sections can induce other types of complications, in particular in the mother. The present invention provides an obstetrical instrument which is an improvement over the forceps and spatulas known from the prior art.

SUMMARY OF THE INVENTION

The present invention relates to an obstetrical instrument, in particular of the forceps type, for the extraction by pulling a fetus during childbirth including two branches, each branch being equipped at one end with a gripping handle and at the other end with cephalic blades and such that, according to the invention, the instrument comprises one measurement module per blade and means for connection between the measurement module and the blade, said measurement module including:
first pressure measurement means capable of measuring the pressure exerted by said blade on the fetus,
second means for measuring the positioning of the obstetrical instrument in space,
power supply means,
means for transmitting the measurements to a processing unit.

The present invention also aims at protecting an assistance device including an obstetrical instrument as mentioned above and further including a processing unit with first processing means for calculating the exerted pressure and comparing it with at least one maximum pressure threshold and/or one maximum pressure threshold per unit of time.

Advantages Provided

A first purpose of the present invention is to overcome all or part of the technical problems related to the aforementioned prior art.

Another purpose of the present invention is to provide an obstetrical instrument allowing to continuously monitor the pressure exerted on the fetus and the path of the forceps.

Another purpose of the present invention is to provide an obstetrical instrument including independent measurement modules of the forceps, and in particular which can be added and removed manually.

Another purpose of the present invention is to provide measurement modules that can be adapted to a wide variety of gripping forceps or clamps or spatulas.

Another purpose of the present invention is to provide waterproof and washable measurement modules.

Another purpose of the present invention is to provide an assistance device allowing to notify the practitioner about pressure threshold crossing or significant variations in the fetal extraction path compared to typical extraction patterns.

Another purpose of the present invention is to provide an assistance device allowing to measure the displacement of the instrument after each pull.

Another purpose of the present invention is to provide an assistance device allowing to record the contractions and the rate of contraction in real time.

Another purpose of the present invention is to provide an assistance device allowing to record the extraction parameters in order to allow a subsequent analysis of the childbirth operation.

BRIEF DESCRIPTION OF THE DRAWINGS

The present invention will be better understood upon reading a detailed exemplary embodiment with reference to the appended figures, provided by way of non-limiting example, among which.

DEFINITIONS

The term "obstetrical instrument" defines, within the meaning of the present invention, a forceps in particular with crossed branches such as a Tarnier or Pajot forceps, with converging branches such as a Suzor forceps or spatulas such as Thierry spatulas. The term further defines any instrument allowing the extraction of a fetus and having an area intended to be applied in pressure to the head of the fetus and comprises in particular various types of gripping forceps.

DETAILED DESCRIPTION OF EMBODIMENTS

Figure 1:
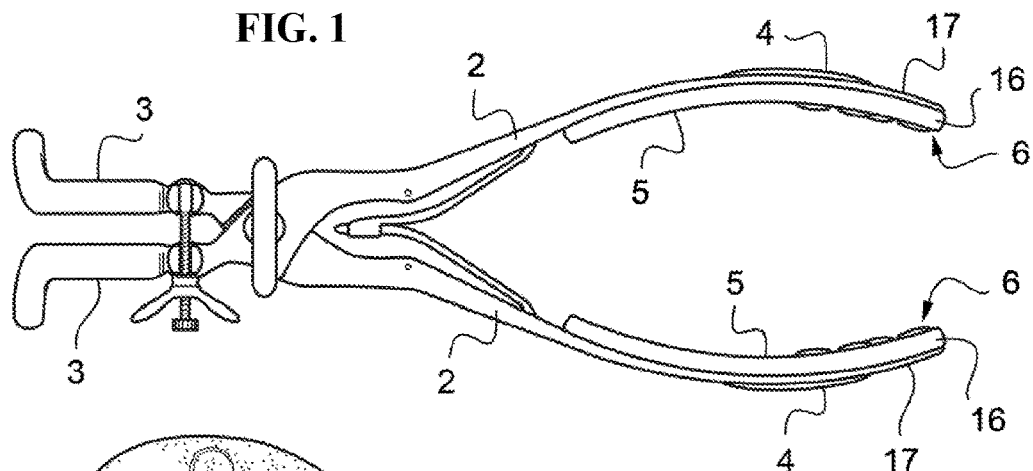
FIG. 1 shows an exemplary schematic embodiment of an obstetrical instrument according to the invention.

The present invention aims at protecting an obstetrical instrument 1 as shown in FIG. 1.

This obstetrical instrument 1 includes two branches 2, each branch 2 being equipped at one end with a gripping handle 3 and at the other end with cephalic blades 4.

Figure 2A:
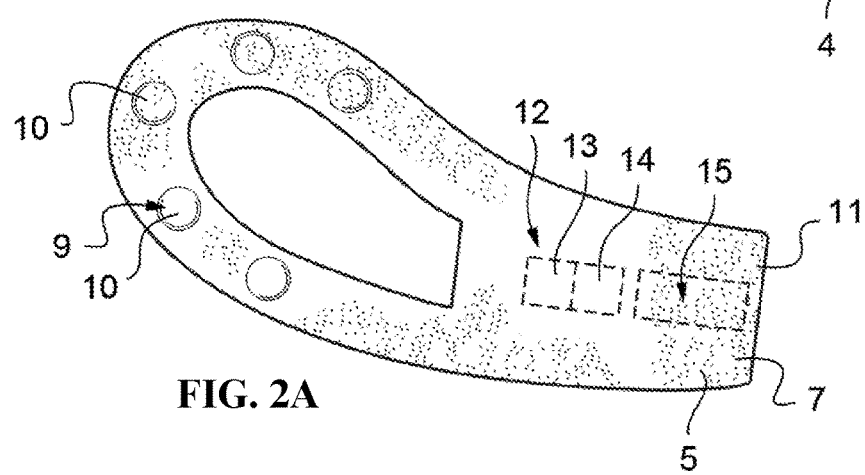
FIGS. 2A and 2B show a schematic and perspective view of a measurement module in accordance with the invention, respectively external face and internal face.
Figure 2B:
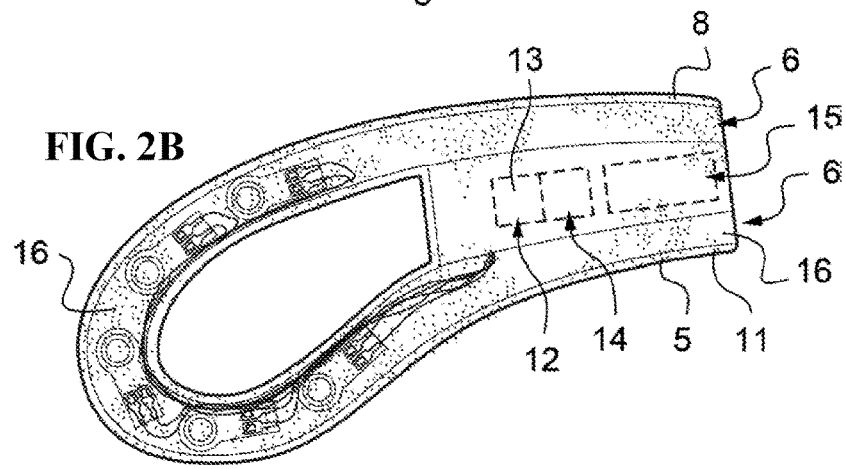
Figure 3:
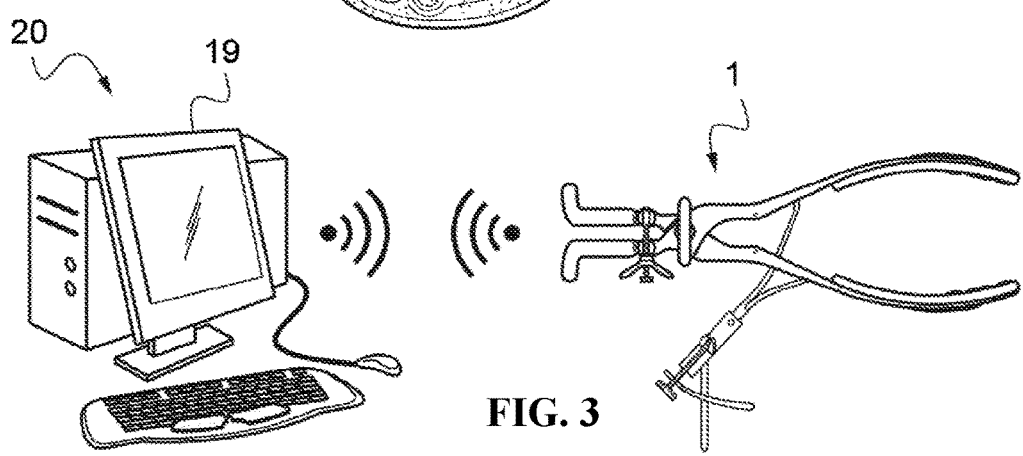
FIG. 3 shows a schematic and perspective view of a device.

According to the invention, the instrument 1, produced in the example of FIGS. 1 to 3 in the shape of a forceps, further comprises a measurement module 5 for each blade 4 and connection means 6 between the measurement module 5 and the blade 4.

Referring to FIGS. 2A and 2B, respectively showing the external 7 and internal 8 faces of the measurement module 5, said measurement module 5 including first pressure measurement means 9 can be seen, capable of measuring the pressure exerted by the blade 4 on the fetus.

In the embodiment of the appended figures, these first measurement means 9 include several point sensors 10 distributed over the external face 7 of each measurement module 5. These sensors 10 may in particular be made from piezo-resistive components. These sensors 10 are encapsulated in the casing 11 surrounding the measurement module 5. In order to allow a good measurement of the pressure, the sensors are disposed in a slightly elevated manner relative to the mean plane of the external face 7.

Advantageously, the elevation will be comprised between 0.1 and 1 mm and the casing will be made of a flexible material so that when positioning the instrument 1, there is necessarily a contact between the sensors and the fetus and at the same time a slight crushing of the sensors 10 so that the pressure exerted by the instrument 1 is distributed over the surface of the external face 7 and not only on the sensors 10.

According to another embodiment, the first pressure measurement means 9 include a single sensor 10. This sensor 10 is advantageously distributed over at least 50% of the surface of the groove, preferably of the piezo-resistive type.

Each measurement module 5 further includes second means 12 for measuring the positioning in space of the obstetrical instrument 1.

These second measurement means 12 are preferably produced by an inertial platform 13. In an advantageous embodiment, each measurement module 5 of a pair of modules 5 equipping an instrument 1 comprises an inertial platform 13. This disposition allows to ensure a greater precision in the displacement of the instrument 1 by reducing the extent of any drift at an inertial platform 13. However, in another embodiment, it is also possible to provide, depending on the precision of the inertial platform 13 and the precision required for the measurement, only one inertial platform 13 for the pair of measurement modules 5.

The measurement modules 5 further include power supply means 14 and means 15 for transmitting measurements to a processing unit. These power supply means 14 will be produced conventionally from cells or batteries. The measurement transmission means 15 will advantageously comprise a Bluetooth type transmitter.

Referring more particularly to FIG. 2B, an exemplary embodiment of the connection means 6 allowing the measurement module 5 to be clipped onto the blade 4 is shown. This feature is particularly advantageous since it allows to position the measurement module 5 on standard forceps.

Clipping also allows to remove and reposition the measurement module 5 from the cephalic blade 4 without tools to carry out any maintenance, replacement or else washing operations of the measurement module 5.

To this end, as shown in FIG. 2B, the connection means 6 include a flexible groove 16 at each measurement module 5. This groove 16 allows the insertion and retention of the edges 17 of the cephalic blade 4.

Referring this time to FIG. 3, an assistance device 18 is shown, this assistance device 18 comprises an obstetrical instrument 1 and a processing unit 19.

The processing unit 19 will allow to calculate data useful for the practitioner.

The processing unit 19 thus includes first processing means for calculating the exerted pressure and comparing it with at least one maximum pressure threshold and/or a maximum pressure threshold per unit of time.

According to an advantageous embodiment, the first processing means comprise a first threshold S1 corresponding to an instantaneous pressure in the standards and a second threshold S2 corresponding to a high instantaneous pressure and a third threshold corresponding to a critical instantaneous pressure.

The processing means perform the comparison between either the maximum pressure exerted on a sensor 10 among all the sensors or an average of the pressures exerted on the sensors 10 and the threshold values S1, S2 and S3.

The assistance device 18 further comprises display and/or alarm means 20 corresponding to the results of the processing unit. The processing unit 19 transmits to these display and/or alarm means 20 the crossing of instantaneous pressure or continuous pressure threshold.

According to a simplified embodiment, the first processing means include a single threshold corresponding to an indication of too high instantaneous pressure on the fetus.

According to another advantageous embodiment, the first processing means comprise a threshold Sc corresponding to a maximum admissible pressure threshold over a given time.

If the threshold Sc is exceeded, a specific information will be displayed on the display means 20 and/or an alert will be transmitted by the alarm means.

The assistance device 18 further comprises second processing means for calculating an extraction path from the data of the second measurement means and comparing the path with positioning data from the database.

To this end, the assistance device 18 records the displacement of the forceps from the positioning coordinates of the forceps on the fetus. The database comprises a typical extraction path composed of two straight-line segments of respective lengths L1 and L2 forming therebetween an angle α. The second processing means allow to follow the displacement of the forceps corresponding to the fetal extraction path and to compare it with the typical extraction path. The second processing means then allow to indicate when the length L1, to within a margin, is reached and to indicate whether the angle α between the two straight-line segments, to within a margin is respected.

The processing unit also advantageously includes third processing means for identifying from the first measurement means the frequency of contraction. These processing means allow to carry out an analysis of the measured pressures and to find in the pressure variations those representative of a contraction, then to store the time information relating to these contractions to determine their frequency.

Of course, other features of the invention could also have been considered without departing from the scope of the invention defined by the claims below.

The invention claimed is:

1. An obstetrical instrument of a forceps type to extract a fetus by pulling during a childbirth, the obstetrical instrument comprising: two branches, each branch being equipped with a gripping handle at a first end and with a cephalic blade at a second end; one measurement device per cephalic blade and a flexible casing surrounding each measurement device, each flexible casing comprising a connector between each measurement device and respective cephalic blade, said each measurement device comprising: a pressure measurement instrument configured to measure a pressure exerted by the respective cephalic blade on the fetus; a position measurement instrument to measure a positioning of the obstetrical instrument; a power supply means; a transmitter to transmit measurements to a processing unit; and wherein each connector is configured to clip each flexible casing onto an exterior face of the respective cephalic blade and to remove and reposition said each flexible casing from the respective cephalic blade without the use of any tool, and said each connector comprises a flexible groove to enable insertion and retention of edges of the respective cephalic blade.

2. The obstetrical instrument of claim 1, wherein each pressure measurement instrument comprises a plurality of point sensors distributed over an external face of the respective measurement device.

3. The obstetrical instrument of claim 1, wherein each pressure measurement instrument comprises a sensor distributed over at least 50% of a surface of the flexible groove.

4. The obstetrical instrument of claim 1, wherein each pressure measurement instrument comprises at least one piezo-resistive type sensor.

5. The obstetrical instrument of claim 1, wherein each position measurement instrument comprises an inertial platform.

6. An assistance device comprising the obstetrical instrument of claim 1, further comprising the processing unit, the processing unit configured to calculate the pressure exerted by one of the cephalic blades on the fetus and to compare the pressure exerted to at least one of a maximum instantaneous pressure threshold and a maximum pressure threshold per unit of time.

7. The assistance device of claim 6, wherein the processing unit is configured to calculate an extraction path from the positioning measurement and to compare the extraction path to positioning data from a database.

8. The assistance device of claim 6, wherein the processing unit is configured to identify a frequency of contraction from the pressure measurement.

9. The assistance device of claim 6, further comprising at least one of a display to display and an alarm to alert results of the processing unit.

* * * * *